United States Patent [19]
Bronstein et al.

[11] Patent Number: 5,843,681
[45] Date of Patent: *Dec. 1, 1998

[54] DIOXETANE COMPOUNDS FOR THE CHEMILUMINESCENT DETECTION OF PROTEASES, METHODS OF USE AND KITS THEREFORE

[75] Inventors: Irena Bronstein, Newton; Brooks Edwards, Cambridge; Christopher Martin, Belmont; Alison Sparks, North Andover; John C. Voyta, Sudbury, all of Mass.

[73] Assignee: Tropix, Inc., New Bedford, Mass.

[*] Notice: The term of this patent shall not extend beyond the expiration date of Pat. No. 5,591,591.

[21] Appl. No.: 728,990

[22] Filed: Oct. 11, 1996

Related U.S. Application Data

[63] Continuation of Ser. No. 385,788, Feb. 9, 1995, Pat. No. 5,591,591.

[51] Int. Cl.⁶ ........................ G01N 33/573; C07D 321/00
[52] U.S. Cl. .................. 435/7.4; 435/6; 530/330; 530/331; 530/807; 548/526; 549/264; 549/332
[58] Field of Search ................... 435/7.4, 6; 549/332, 549/264; 530/331, 807, 330; 548/526

[56] References Cited

U.S. PATENT DOCUMENTS

| | | | |
|---|---|---|---|
| 4,931,223 | 6/1990 | Bronstein et al. | 436/537 |
| 4,952,707 | 8/1990 | Edwards et al. | 549/221 |
| 4,956,477 | 9/1990 | Bronstein et al. | 549/221 |
| 4,978,614 | 12/1990 | Bronstein | 435/21 |
| 5,089,630 | 2/1992 | Bronstein et al. | 549/220 |
| 5,112,960 | 5/1992 | Bronstein et al. | 536/26 |
| 5,145,772 | 9/1992 | Voyta et al. | 435/7.4 |
| 5,220,005 | 6/1993 | Bronstein | 549/221 |
| 5,326,882 | 7/1994 | Bronstein et al. | 549/16 |
| 5,330,900 | 7/1994 | Bronstein et al. | 435/6 |
| 5,336,596 | 8/1994 | Bronstein et al. | 435/6 |

*Primary Examiner*—Mary E. Ceperley
*Attorney, Agent, or Firm*—Oblon, Spivak, McClelland, Maier & Neustadt, P.C.

[57] ABSTRACT

1,2-dioxetane compounds bearing a proteolytic enzyme specific amino acid or peptide are provided, which amino acid or peptide can be removed by action of the corresponding protease. When the amino acid or peptide is removed, the 1,2-dioxetane decomposes with chemiluminescence, the generation of light providing a rapid, ultra-sensitive and convenient means for detecting the presence of the protease in the sample being inspected. The amount of light generated, or degree of chemiluminescence, can be correlated with the amount of protease present. Immunoassays, as well as DNA hybridization and DNA probe assays are provided.

16 Claims, 3 Drawing Sheets

DIOXETANE COMPOUNDS FOR THE CHEMILUMINESCENT DETECTION OF PROTEASES, METHODS OF USE AND KITS THEREFORE

This is a Continuation of application Ser. No. 08/385,788 filed on Feb. 9, 1995, now U.S. Pat. No. 5,591,591.

BACKGROUND OF THE INVENTION

1. Field of the Invention

This invention pertains to chemiluminescent compounds, their use in assays for the detection of proteases, and kits comprising the compounds and other elements used in protease detection assays. Specifically, dioxetane compounds bearing a proteolytic enzyme-specific amino acid or peptide which, when removed by enzymatic reaction, causes the dioxetane to decompose and chemiluminesce, is provided. These compounds, when added to a sample suspected of containing the protease, provide a rapid, ultrasensitive and convenient means for detecting the presence of the protease in the sample. The amount of light generated, or degree of chemiluminescence, can be correlated with the amount of protease present.

BACKGROUND OF THE INVENTION

Applications naming one or more of the inventors herein, as inventors, and assigned to Tropix, have clearly established 1,2-dioxetanes as chemiluminescence compounds which can be used as reporters in ultrasensitive assays that can be conducted quickly, without resort to exotic conditions or elaborate apparatus, for the detection of a variety of biological materials. Among these are U.S. Pat. Nos. 4,931,223; 4,931,569; 4,952,707; 4,956,477; 4,978,614; 5,032,381; 5,145,772; 5,220,005; 5,225,584; 5,326,882; 5,330,900 and 5,336,596. Other patents commonly assigned with this application have issued, and still other applications are pending. Together, this wealth of patent literature addresses 1,2-dioxetanes, stabilized by a typically polycyclic group, preferably spiroadamantane bonded to one of the carbons of the dioxetane ring, and a moiety bonded to the remaining carbon of the dioxetane ring which is electron sensitive, such that deprotection of the electron sensitive moiety, typically an aryl group, more preferably a phenyl or naphthyl group, leads to an anion, generally an oxyanion, which is unstable, and decomposes. Through decomposition, the O—O bond is broken, and a photon is generated. The same carbon atom to which this electron sensitive moiety is bonded may bear an alkoxy or other electron-active group. Methoxy is a preferred moiety.

The first of the dioxetanes of this class commercialized was 3-(4-methoxy-spiro[1,2-dioxetane-3,2'-tricyclo[3.3.1.1$^{3,7}$]decan]-4-yl)phenyl phosphate, particularly the disodium salt, generally known as AMPPD. This compound has been commercialized by Assignee of this application, Tropix, Inc., as well as a company of Detroit, Mich., Lumigen, Inc. The primary inventor of Lumigen, A. Paul Schaap, has been granted several patents on related technology.

Superior performance can be obtained by selective substitution on the spiroadamantane ring. Substitution, at either bridgehead carbon, with an electron-active species, such as chlorine, improves reaction speed and signal-to-noise ratio (S/N). The chlorine-substituted counterpart of AMPPD, CSPD, has been widely commercialized by Tropix, Inc. of Bedford, Mass. "Third-generation" dioxetane compounds of similar structure, wherein the phenyl or naphthyl moiety also bears an electron-active substituent, such as chlorine, offer further improvements in performance, and have been commercialized by Tropix, Inc. The phosphate moieties is available under the trademarks CDP and CDP-Star.

A common characteristic of all these dioxetanes is the blocking or masking group on the phenyl or naphthyl moiety. Groups which are enzyme-specific substrates are employed, such that, when admixed with the enzyme, the blocking group is removed by the enzyme, leaving an electron rich oxygen moiety attached to the phenyl or naphthyl substituent. Typically, this blocking group has been a phosphate, although other blocking groups, such as a galactoside have also been used. Representative blocking groups are set forth in the patents listed above, which are incorporated herein by reference. These blocking groups have been substrates for enzymes which are specific for the blocking group, the enzymes either being selected as enzymes of interest or potential interest in a biological fluid, or non-endogenous enzymes which may be coupled to a particular target moiety of the sample, their triggering of the dioxetane to generate light being thus evidence of the analyte in the sample to which the non-endogenous enzyme is coupled. Alkaline phosphatase has been the dominant enzyme of interest as a triggering agent.

The existing literature on dioxetanes does not describe a triggerable dioxetane, that is, a dioxetane which can be "deprotected" to induce decomposition and chemiluminescence that can be used to detect, or be triggered by, proteolytic enzymes, that is, peptidases. These enzymes are involved in the life cycle of proteins. Further, proteolytic enzymes are also involved in the processing of proteins, hormones, receptors, growth factors, fertilization, activation of regulatory proteases involved in blood coagulation, fibrinolysis and the complement reaction, and other cellular functions. Thus, the presence or absence of a particular proteolytic enzyme in a biological sample may well indicate the presence or absence of a particular disease state, pathogenic condition or organic syndrome. Families of proteolytic enzymes include serine proteases (chymotrypsin and subtilisin), cysteine proteases (papain), aspartic proteases (penicillopepsin) and metalloproteases (carboxypeptidase and thermolysin).

In addition to being of particular interest as organic moieties that constitute diagnostic markers, protease enzymes are also of considerable interest as enzyme labels, and are used in detergent production and leather processing. Examples of diagnostic protease markers include cathepsin B (cancer), cathepsin G (emphysema, rheumatoid arthritis, inflammation), cathepsin L (cancer), elastase (emphysema, rheumatoid arthritis, inflammation), plasminogen activator (thrombosis, chronic inflammation, cancer), and urokinase (cancer). The use of alkaline proteases in detergents is expected to increase. Assays for protease detection are therefore needed to monitor protein stability in various biological and commercial processes.

Known protease assay conditions are listed in the following table:

| Protease | Assay Conditions |
| --- | --- |
| acylaminoacyl peptidase | Ac-Ala-p-nitroanilide in Tris HCl, pH 7.5, 37° C. |
| aminopeptidase M | L-Leu-p-nitroanilide in 60 mM Na phosphate buffer, pH 7–7.5, 37° C. |

3

-continued

| Protease | Assay Conditions |
|---|---|
| cathepsin B | Bz—Phe—Arg—NMec, pH 5.5–6.0, 37° C. |
| cathepsin G | MeO—Suc—Ala—Ala—Pro—Phe-p-nitroanilide, pH 7.5, 25° C. |
| cathepsin L | Cbz—Phe—Arg—NMec in 340 mM Na acetate, 60 mM acetic acid, 4 mM disodium EDTA, pH 5.5, 8 mM dithiothreitol, 30° C. |
| elastase | Suc—(Ala)$_3$-p-nitroanilide, 0.05% Triton X-100 in plastic tubes, pH 7.8, 25° C. |
| subtilisin | denatured hemoglobin degradation, pH 7–8 |
| plasminogen activator | Val—Leu—Lys-p-nitroanilide in 50 mM Tris-HCl, pH 8.5, 37° C. |
| urokinase | Val—Phe—Lys-p-nitroanilide in 50 mM Tris-HCl, pH 8.5, 37° C. |

Some of the known and potential applications for proteolytic enzymes are listed in the following table:

| Protease | Applications |
|---|---|
| Aminopeptidase | detection of gram-neg bacteria |
| Cathepsin B | cancer marker |
| Cathepsin G | emphysema, rheumatoid arthritis, inflammation marker |
| Cathepsin L | cancer marker |
| Elastase | emphysema, rheumatoid arthritis, inflammation marker |
| Subtilisin | used in leather processing as a depilatory, detergents, protein hydrolysate production (e.g. Optimase and Opticlean enzymes by Solvay Enzymes), |
| Plasminogen Activator | thrombosis, chronic inflammation, cancer marker |
| Urokinase | cancer marker |
| General | Protease screen, screening of protein formulations for the presence of proteases. Sensitive detection of DNA in solution and on blots utilizing thermophilic enzymes such as thermolysin which would enable the incorporation of the enzyme label during the DNA preparation procedure such as high temperature denaturation and PCR amplification. |

See also generally Proteolytic Enzymes—A Practical Approach, IRL Press, pp.-233–40 (1989).

Known Protease Assay Methods

The basic methods of the detection of proteolytic enzymes consist of an enzymatic reaction with a suitable substrate and the detection of the product of this reaction. Thus, a known protease will cleave a synthetic peptide which is a substrate for such enzyme. Synthetic substrates are amino acids and peptides. Specific substituents are added to the α-NH$_2$ or α—COOH groups to either block the amino or the carboxyl to produce a substrate which can be recognized and cleaved by a specific protease. Additionally, the added group may add a "signaling" property to a substrate such that the products of the substrate-enzyme reaction can be detected and monitored by absorption or fluorescence spectrometry.

There are several commercially available assays for proteolytic enzymes. Promega offers a PepTag™ Protease Assay. This is a qualitative assay which detects the proteolysis of small dye-linked peptides. Since the digestion of these peptides changes their molecular weight and charge, they can be detected using agarose gel electrophoresis. This assay, however, is cumbersome, not sensitive and not quantitative. There are also several fluorogenic substrates for proteolytic enzymes available from Sigma, Calbiochem and Molecular Probes.

Accordingly, it remains an object of those of skill in the art to provide a quick, reliable and sensitive assay for the detection of proteolytic enzymes, either as markers, commercial indicators, or labels, that can be both qualitative and quantitative. It is a further objection of those of skill in the art to provide dioxetane compounds which can be triggered by proteolytic enzymes to decompose and chemiluminesce, in a fashion analogous to those reflected in the literature, which undergo decomposition from the oxyanion moiety.

SUMMARY OF THE INVENTION 1,2-dioxetanes of the following general formula I can be used to detect the presence of proteolytic enzymes in a sample.

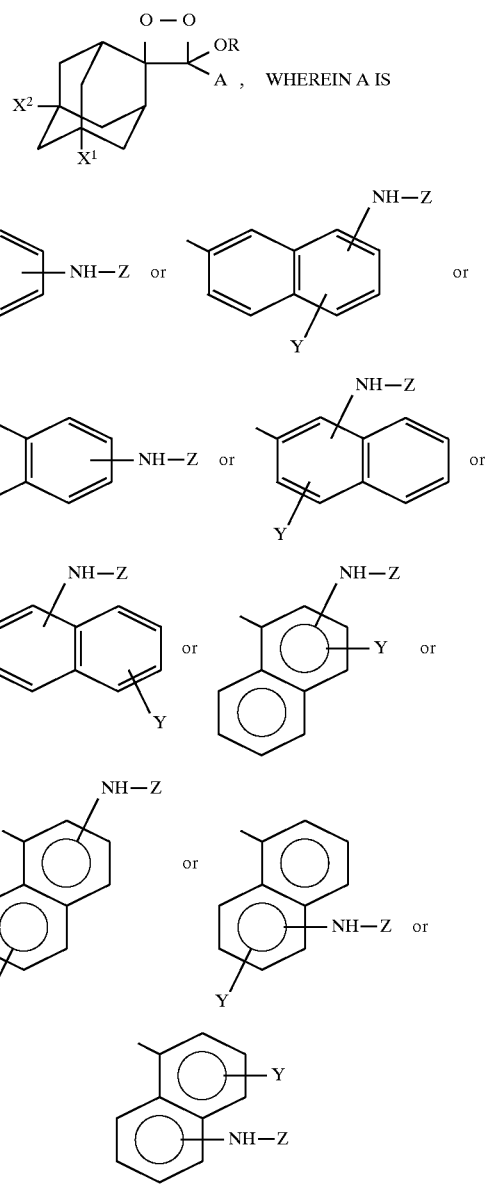

Wherein $X^1$, $X^2$ and Y are independently hydrogen or an electron active substituent, wherein R is an alkyl, straight-chain or branched chain of 1–20 carbon atoms or cycloalkyl or polycycloalkyl of 3–20 carbon atoms, and wherein Z is an amino acid, or a polypeptide, wherein Z is an enzyme-specific substrate. These dioxetanes are stable under storage conditions, and sufficiently soluble in water or an aqueous preparation so as to serve as a chemiluminescent reporter molecule for detection of proteolytic enzymes which cleave the enzyme-specific substrate Z. When the Z group is removed, the arylamine decomposes, breaking the O—O bond of the dioxetane ring and generating chemiluminescence as in the case of conventional 1,2-dioxetanes triggered through the formation of the oxyanion addressed in the literature. To improve solubility, any one or more of $X^1$, $X^2$ or Y can be selected to be a solubilizing agent, that is, an agent which improves hydrogen-bonding, so as to improve the solubility of the dioxetane reporter molecule in the sample, which is generally aqueous in nature, particularly where biological assays are being conducted. For aqueous solubility, R is preferably 6 carbon atoms or less. Certain commercial processes may require organic preparations and organic solvents. In these cases, R may be of greater size, and $X^1$, $X^2$ and Y selected so as to improve solubility in the selected solvent.

Z in the above formula is selected to be a proteolytic enzyme-specific substrate. By this, it is intended that Z be particularly formulated to be a substrate which is cleaved by a specific proteolytic enzyme, or class of enzymes, such that other enzymes likely to be in the sample assayed will not cleave the Z moiety, and thus, any chemiluminescence detected will be traceable directly to the presence of the enzyme itself. The invention is not limited to any specific amino acid or peptide sequence, and is open to both commercially available peptide sequences and groups to be developed for specific assays. It should be noted that certain proteolytic assays are specific for a single amino acid. In this situation, Z can be confined to a single amino acid. Once the peptide or amino acid is removed, the resulting dioxetane amine will decompose with chemiluminescence, just as in the case of the oxyanions of the existing dioxetane literature. The amount of chemiluminescence can be correlated with the amount of enzyme.

BRIEF DESCRIPTION OF THE FIGURES

FIG. 3 provides information on the experiment reflected in FIG. 2, with further incubation for one hour at 45° C.

DETAILED DESCRIPTION OF THE INVENTION

Figure 1:
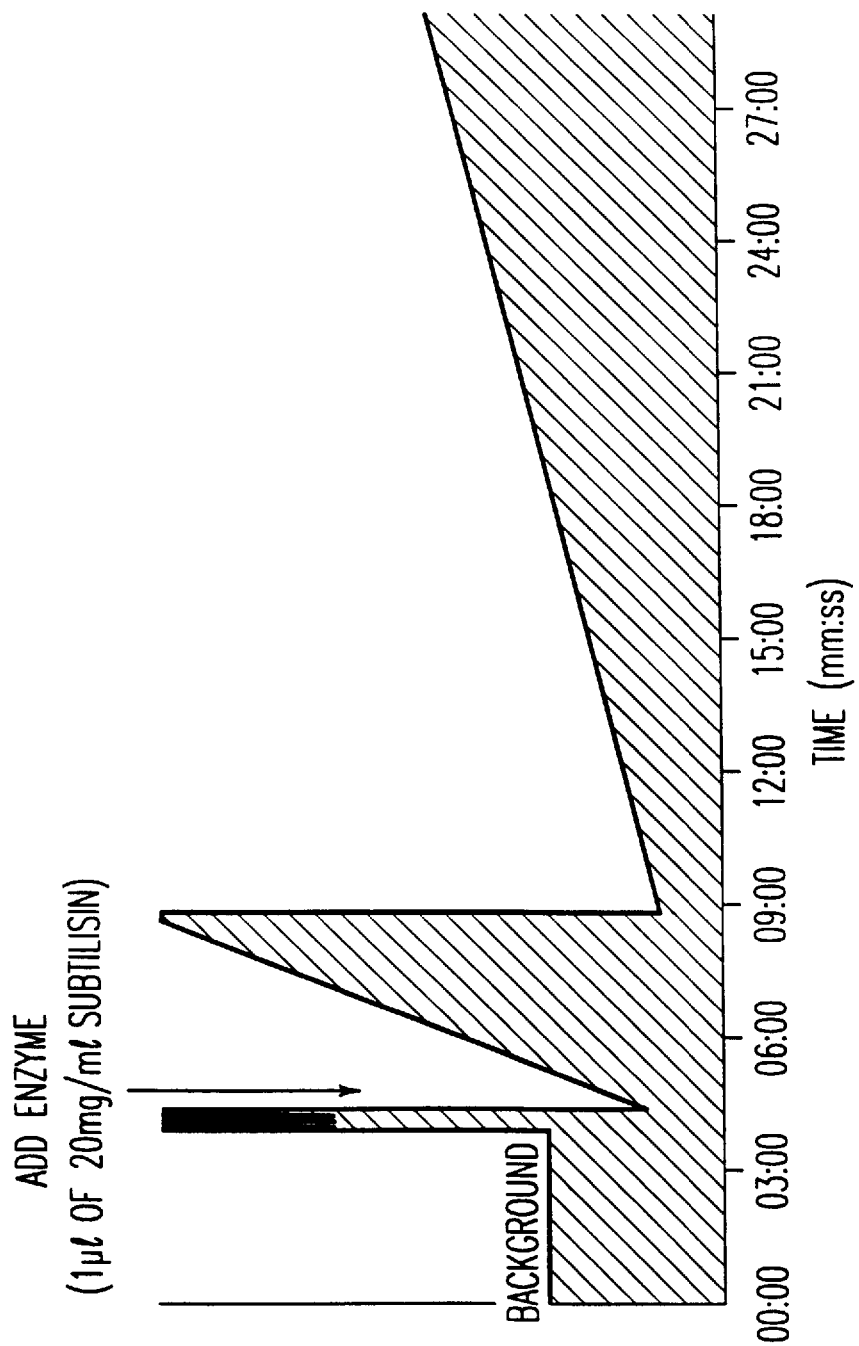
FIG. 1. Chemiluminescence trace obtained by subtilisin triggering of 1,2-dioxetane subtilisin-specific substrate.

The dioxetanes claimed herein begin with starting materials akin to those employed for the phenoxy-substituted dioxetanes of the literature. Thus, the chemical structure of the dioxetane compounds claimed herein is analogous to that of the phenoxydioxetanes of the prior art, save for the fact that the oxygen moiety linked to the phenyl group substituted on the dioxetane, or naphthyl group substituted on the dioxetane, is replaced with an amino group. The compounds have the formula

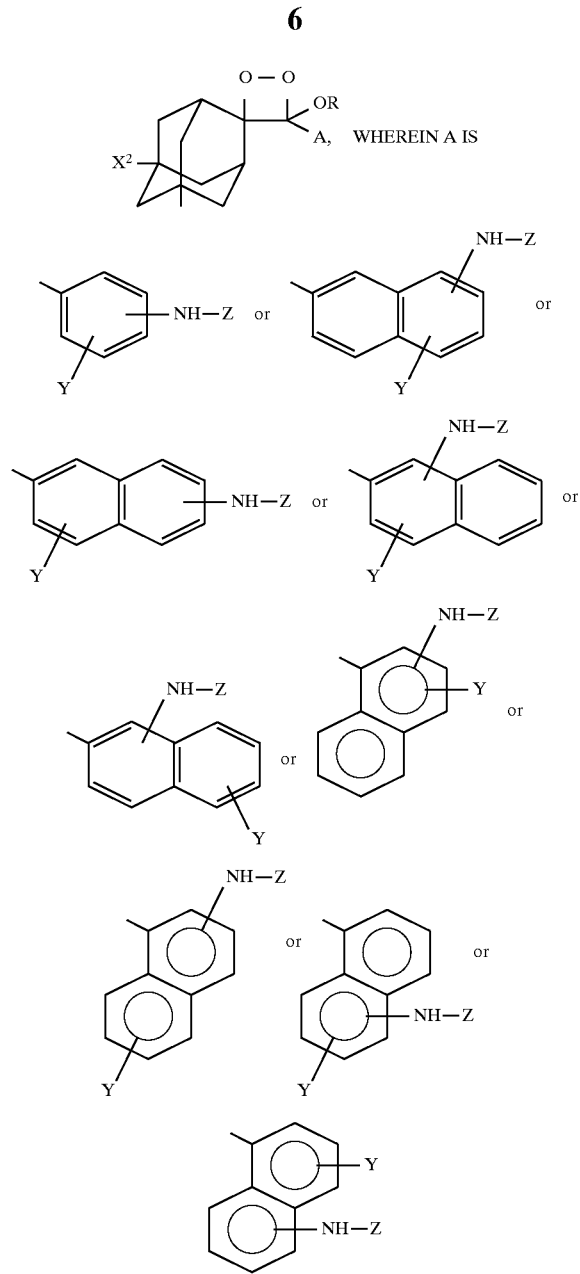

wherein $X^1$, $X^2$ and Y are independently H or an electron active (electron withdrawing or electron donating) moiety. If the group is an electron active group, it may also be selected to improve the solubility of the dioxetane in the solvent or medium selected. Most commonly, the sample to be assayed is prepared in an aqueous medium, and accordingly, the solubilizing moiety or moieties will be those that facilitate hydrogen bonding. Depending whether $X^1$, $X^2$ and Y are selected as hydrogen or electron active, the identity may affect, in addition to solubility, half-life (T½) of the decomposition reaction, chemiluminescent yield, and signal to noise ratio (S/N). Suitable substituents and their impact on the dioxetane chemiluminescence, are discussed in connection with phenoxy-substituted dioxetanes and disclosed and claimed in U.S. Pat. No. 5,330,900. Thus, each of the substituents at the bridge-head carbons on the adamantane ring may individually represent, in addition to hydrogen, a hydroxyl group, a halosubstituent, a hydroxy lower alkyl group, a halo lower alkyl group, a phenyl group, a halo phenyl group, an alkoxy phenyl group, a hydroxy alkoxy group, a cyano group, or an amide group, Similarly, the identity of Y may be hydrogen or electron active. If selected without regard to solubility characteristics, exemplary identities for Y include Cl, OM, OAr, $NM_3+$, NHCOM, $NMCOM^1$, NHCOAr, NHCOOAr, NHCOOM, $NMCOOM^1$, $CM_3$, $NO_2$, COOM, COOAr, $NHSO_2OM$, $NHSO_2Ar$, $CF_3$, Ar, M, $SiM_3$, $SiAr_3$, $SiArM_2$, $SO_2$, NHCOM, $SO_2NHCOAr$, $SO_2M$, $SO_2Ar$, SM and SAr wherein M and $M^1$ are independently C1-6 alkyl, and Ar is phenyl or naphthyl. A preferred substituent is chlorine, methoxy, alkyl or amido. Compounds of this type, bearing a phenoxy, rather than a phenyl amine substituent are disclosed and claimed in pending U.S. patent application Ser. No. 08/057,903. The same is incorporated herein by reference.

The point of substitution of Y and the NH-Z moiety on the aryl ring may influence the chemiluminescence obtained and the $T_{1/2}$ of the resulting dioxetane. Where the dioxetane bears a phenyl substituent, the preferred point of substitution for NH-Z is meta with respect to the point of attachment to the dioxetane, and where substituting on a naphthyl moiety, the NH-Z moiety should be at a position disjoint from the point of attachment to the dioxetane moiety. Preferred positions for Y when not hydrogen, are positions other than ortho with respect to the point of attachment to the dioxetane.

The identity of moiety Z is not specifically limited, save that it must be an enzyme-cleavable group, such that when admixed with a sample containing the enzyme of interest, the enzyme cleaves the moiety Z, causing the dioxetane amine to undergo spontaneous decomposition, generating light. A large number of substrates for proteolytic enzymes suitable as candidates for moiety Z are commercially available, and others have been identified. Z is typically an amino acid or peptide, although some proteases recognize only amino acids or peptides with blocking groups, such as N-carbobenzoxy (N-Cbz or N-Z), N-succinyl (N-suc), N-methoxysuccinyl (N-MeOsuc), N-acyl (N-Ac) or N-benzoyl (N-Bz). Z is an amino acid, peptide, or the same protected with a blocking group, such that the protease recognizes Z as a cleavage site. The following identities for moiety Z are exemplary only, and are not intended to limit the scope of the invention.

| Protease | (Amino Acid or Peptide Z—) |
|---|---|
| Alzheimer's Disease (Amyloid A4-generating enzymes) | Cbz—Val—Lys—Met— |
| Aminopeptidase | Arg— |
| | Ala— |
| | Ala—Ala—Phe— |
| | Glu— |
| | Gly—Pro—Leu— |
| | Gly—Pro—Met— |
| | Leu— |
| Cathepsin B | Arg— |
| | Cbz —Arg—Arg— |
| | Cbz—Phe—Arg— |
| | Bz—Arg— |
| | Suc—Ala—Ala—Pro—Phe |
| | Cbz—Ala—Arg—Arg— |
| Cathepsin C | Gly—Phe— |
| | Ala—Arg— |
| | Bz—Arg—Gly—Leu— |
| | Gly—Arg— |
| Cathepsin D | Bz—Arg—Gly—Phe—Phe—Pro— |
| Cathepsin G | Suc—Ala—Ala—Phe— |
| | Suc—Phe—Leu—Phe— |
| | Suc—Val—Pro—Phe— |
| | MeOSuc—Ala—Ala—Pro—Met— |

-continued

| Protease | (Amino Acid or Peptide Z—) |
|---|---|
| Cathepsin H | Arg— |
| | Leu— |
| Cathepsin L | Cbz—Phe—Arg— |
| Elastase | Ac—Ala—Ala—Ala |
| | Suc—Ala—Ala—Ala— |
| | Boc—Ala—Ala—Ala— |
| | Suc—Ala—Ala—Val— |
| | Suc—Ala—Pro—Ala— |
| | Ac—Ala—Pro—Ala— |
| | Suc—Ala—Ala—Pro— |
| | Ac—Ala—Ala—Pro—Ala— |
| | Boc—Ala—Ala—Pro—Ala— |
| | Glu—Ala—Ala—Pro—Leu— |
| | Suc—Ala—Ala—Pro—Met— |
| | MeOSuc—Ala—Ala—Pro—Val— |
| | Boc—Ala—Ala—Pro—Val— |
| | Suc—Leu—Leu—Val—Tyr— |
| | Pro—Phe—Arg— |
| | Cbz—Gly— |
| Endopeptidase | Cbz—Gly—Gly—Leu— |
| Subtilisin | Cbz—Ala—Ala—Leu— |
| | Boc—Gly—Gly—Leu— |
| | Cbz—Gly—Gly—Leu |
| Thermolysin | Abz—Ala—Ala—Phe—Phe— |
| | Cbz—Phe—Arg— |
| | Cbz—Phe—Pro—Arg— |
| tPA | Cbz—Gly—Gly—Arg— |
| | Bz—Val—Gly—Arg— |
| | Boc—Val—Gly—Arg— |
| Urokinase | Cbz—Gly—Gly—Arg— |
| | Glt—Gly—Arg— |
| | Gly—Arg— |
| | Cbz—Val—Gly—Arg— |

Key:
Abz  2-aminobenzoyl
Ac   acetyl
Bz   benzoyl
Glt  glutaryl
Suc  succinyl
Cbz  carbobenzoxy
pGlu pyroglutamyl
Abu  2-aminobutyric acid
pyr  pyroglutamic acid There are many commercially available peptides which are substrates for proteolytic enzymes and can be used to append suitable 1,2-dioxetanes to generate chemiluminescent substrates for such enzymes. The list of commercial protease susbtrates is shown in the following table:

| Protease | Substrates |
|---|---|
| Aminopeptidase | Leu—X |
| | Ala—X |
| | Arg—X |
| | Glu—X |
| Cathepsin B | Arg—X |
| | Cbz—Arg—Arg—X |
| | Cbz—Phe—Arg—X |
| | Cbz—Ala—Arg—Arg—X |
| Cathepsin H | Arg—X |
| | Leu—X |
| Cathepsin G | Suc—Phe—Leu—Phe—X |
| | Suc—Val—Pro—Phe—X |
| | Suc—Ala—Ala—Phe—X |
| | Suc—Phe—Pro—Phe—X |
| Cathepsin L | Cbz—Phe—Arg—X |
| Elastase | Ac—Ala—Ala—Ala—X |
| | Suc—Ala—Ala—Val—X |
| | Suc—Ala—Ala—Pro—X |
| | Suc—Ala—Pro—Ala—X |
| | MeOSuc—Ala—Ala—Pro—Val—X |
| Subtilisin | Cbz—Ala—Ala—Leu—X |
| | Cbz—Gly—Gly—Leu—X |

-continued

| Protease | Substrates |
|---|---|
| Urokinase | Cbz—Gly—Gly—Arg—X |
|  | Cbz—Val—Gly—Arg—X |

X = p-nitroanilide, 7-amido-4-methylcoumarin, or 7-amido-4-trifluoromethylcoumarin The specificity of a substrate is dictated by the enzyme's recognition of specific peptide sequences. The specific cleavage sites for proteolytic enzymes are listed in the following table:

| Protease | Specificity | Preferred Sites |
|---|---|---|
| aminopeptidase M | nonspeccific | Ala, Arg, Glu, Leu |
| cathepsin B | basic amino acid | Lys, Arg |
| cathepsin G | aromatic amino acid | Phe, Tyr |
| cathepsin L | Arg | Arg |
| elastase | uncharged nonaromatic | Ala, Val |
| subtilisin | nonspecific | Leu |
| plasminogen activator | capped basic amino acid | Lys, Arg |
| urokinase | basic amino acid | Lys, Arg |

Syntheses of Protease Diozetane Substrates

The following exmaples are representative syntheses of dioxetane protease substrates and should not limit the scope of the claims. N-Cbz and N-Ac are abbreviations for N-carbobenzoxy and N-acetyl respectively.

| Diozetane | Peptide chain | Substrate for |
|---|---|---|
| 3 | Leu—Gly—Gly—N—Cbz | subtilisin |
| 9 | Arg | cathepsins B/H aminopeptidase |
| 10 | Arg—Ala—N—Cbz | trypsin |
| 11 | Arg—Gly—Gly—N—Cbz | tissue plasminogen activator urokinase |
| 12 | Arg—Gly—Val—N—Cbz | urokinase |
| 17 | Ala—Ala—N—Cbz | elastase |
| 18 | (Ala)$_3$—N—AC | elastase |
| 19 | (Ala)$_4$—N—Cbz | elastase |

3- (Methoxytricyclo[3.33.1.1$^{3,7}$]dec-2-ylidenemethyl)-1-anilinyl-Leu-Gly-Gly-N-Cbz(2). Enol ether aniline 1 (206 mg, 0.77 mmol, synthesized as described in SBIR Grant #1 R43 HG00196-01) was dissolved in 4 ml anhydrous dimethylformamide (DMF) and 4 ml anhydrous pyridine (py) under argon. N-Cbz-Gly-Gly-Leu (1.2 g, 3.2 mmol), 1-[3-(dimethylamino)propyl]-3-ethylcarbodiimide HCl (606 mg, 3.2 mmol) and 1-hydroxybenzotriazole (53 mg, 0.4 mmol) were added under argon at room temperature. The reaction was stirred for 1 hr, partitioned between ethyl acetate and water, and the organic layer was washed successively with dilute brine and dilute sodium bicarbonate solutions. The organic layer was dried over NA$_2$SO$_4$, evaporated and purified on a silica gel column (30–100% EtOAc/hexanes) to yield 367 mg (76%) of enol ether peptide 2 as a white foam.

$^1$H NMR (CDCl$_3$, ppm): 0.82 (3H, d, J=6 Hz); 0.86 (3H, d, J=6 Hz); 1.58–1.99 (15H, m); 2.56 (1H, br s); 3.16 (1H, br s); 3.20 (3H, s); 3.88 (1H, m); 3.91 (2H, m); 3.97 (2H, m); 4.65 (1H, br s); 5.03 (2H, s); 5.87 (1H, br s); 6.97 (1H, d, J=7.5 Hz); 7.16 (1H, t, J=8 Hz); 7.24 (5H, s); 7.43 (1H, br s); 7.49 (2H, m); 8.92 (1H, br s)

3-(4-Methoxyspiro[2-dioxetane-3,2'tricyclo[3.3.1.1$^{3,7}$]decan]-4-yl)-1-anilinyl-Leu-Gly-Gly-N-Cbz (3). A solution of enol ether peptide 2 (212.6 mg, 0.34 mmol) and 5,10,15, 20-tetraphenyl-21H,23H-porphine (TPP, 0.6 ml of a 2% solution in CHCl$_3$ by weight) in 10 ml chloroform was irradiated with a 250 W, high pressure sodium lamp at 10° C. while passing a stream of oxygen through the solution. A 5-mil piece of Kapton polyimide film (DuPont) placed between the lamp and the reaction mixture filtered out unwanted UV radiation. Analytical tlc and hplc showed complete dioxetane formation upon irradiating 8 min. The solvent was removed under vacuum at 0° C. and pumped dry. The residual light yellow foam was dissolved in 1 ml acetonitrile (hplc grade) and stored overnight in the freezer to allow crystal formation. The acetonitrile was pipeted off the white precipitate, the precipitate was washed with 1 ml acetonitrile and then dried on high vacuum to give 152 mg (77%) of white crystalline dioxetane 3.

$^1$H NMR (DMSO-d$_6$, ppm): 0.87 (3H, d, J=6.35 Hz); 0.89 (3H, d, J=6.35 Hz); 0.92 (1H, d); 1.19 (1H, d, J=10.8 Hz); 1.44–1.75 (13H, m); 2.07 (1H, br s); 2.90 (1H, br s); 3.10 (3H, s); 3.64 (2H, d, J=6 Hz); 3.76 (2H, d, J=6Hz); 4.44 (1H, m); 5.01 (2H, s); 7.30 (1H, m); 7.33 (5H, m); 7.41 (1H, t, J=7.8 Hz); 7.54 (1H, t, J=6 Hz); 7.74 (1H, d, J=7.8 Hz); 7.88 (1H, br s); 8.10 (1H, d, J=7.8 Hz); 8.17 (1H, m).

3-(Methoxytricyclo[3.3.1.1$^{3,7}$]dec-2-ylidenemethyl)-1-anilinyl-N$^\alpha$, N$^G$, N$^{G1}$-tri-Cbz-L-Arg (4). Enol ether aniline 1 (31 mg, 0.115 mmol) was dissolved in 0.5 ml anhydrous dimethylformamide and 0.5 ml anhydrous pyridine under argon. N$^\alpha$, N$^G$, N$^{G1}$-Tricarbobenzoxy-L-arginine (77 mg, 0.133 mmol), 1-[3-(dimethylamino)propyl]-3-ethylcarbodiimide HCl (25 mg, 0.13 mmol) and a crystal of 1-hydroxybenzotriazole were added under argon at room temperature. The reaction was stirred for 1 hr, stored overnight in the freezer, partitioned between ethyl acetate and water, and the organic layer was washed successively with dilute brine and dilute sodium bicarbonate solutions. The solvent was evaporated to leave enol ether 4 as white crystals (89.5 mg, 94%).

$^1$H NMR (CDCl$_3$, ppm): 1.6–2.0 (16H, m); 2.59 (1H, br s); 3.22 (1H, br s); 3.24 (3H, s); 3.88 (1H, m); 4.03 (1H, m); 4.45 (1H, m); 4.90 (1H, d, J=12 Hz); 5.07–5.21 (6H, m); 6.26 (1H, d, J-7.65 Hz); 7.02 (1H, d, J=7.24 Hz); 7.13–7.37 (18H, m); 8.42 (1H, br s); 9.31 (1H, br s); 9.45 (1H, br s).

3-Methoxytricyclo[3.3.1.1$^{3,7}$]dec-2-ylidenemethyl)-1-anilinyl-L-Ara (5). Dissolve tri-N-Cbz-Arg enol ether 4 in 2.5 ml absolute EtOH, add 5% Pd/C (106 mg) and 1,4-cyclohexadiene (250 μl) and stir in a pressure tube at 70° C. for 2 h. Filter the solution through a celite plug, rinse the plug well with water and evaporate the solution to give the deprotected arginine enol ether 5. This intermediate is used to synthesize arginine enol ether derivatives 6–8 as described below.

3-Methoxytricyclo[3.3.1.1$^{3,7}$]dec-2-ylidenemethyl)-1-anilinyl-Arg-Ala-N-Cbz (6). Arginine enol ether 5 is dissolved in anhydrous dimethylformamide: pyridine (1:1) under argon. N-Carbobenzoxyalanine (1.1 eq), 1-[3-(dimethylamino) propyl]-3-ethylcarbodiimide HCl (1.2 eq), and a crystal of 1-hydroxybenzotriazole are added under argon at room temperature. The reaction is stirred until coupling is complete, partitioned between ethyl acetate and water, and the organic layer is washed successively with dilute brine and dilute sodium bicarbonate solutions. The solvent is evaporated to give N-Cbz-Ala-Arg enol ether 6. Alternatively, coupling can be effected by a mixed anhydride method using an alkylchloroformate such as isobutylchloroformate in the presence of N-methylmorpholine (Smith and Bissell, 1981, U.S. Pat. No. 4,294,923).

3-Methoxytricyclo[3.3.1.1$^{3,7}$]dec-2-ylidenemethyl)-1-anilinyl-Arg-Gly-Gly-N-CBz (7). N-Cbz-Gly-Gly-Arg enol ether 7 is synthesized from enol ether 5 as described for compound 6, where N-carbobenzoxyglycine-glycine is used.

3-Methoxytricyclo[3.3.1.1³,⁷]dec-2-ylidenemethyl)-1-anilinyl-Ara-Gly-Val-N-Cbz (8). N-Cbz-Val-Gly-Arg enol ether 8 is synthesized from enol ether 5 as described for compound 6, where N-carbobenzoxyvaline-glycine is used.

3-Methoxyspiro[1,2-dioxetane-3,2'tricyclo[3.3.1.1³,⁷]decan]-4-yl)-1-anilinyl-L-Arg (9). A solution of arginine enol ether 5 in 1:1 CHCl₃:acetone and 5,10,15,20-tetraphenyl-21H,23H-porphine (TPP, 1.5 ml of a 2% solution in CHCl₃ by weight) is cooled to −78° C. in a dry ice/acetone bath and irradiated with a 250 W, high pressure sodium lamp while passing a stream of oxygen through the solution. A 5-mil piece of Kapton polyimide film (DuPont) placed between the lamp and the reaction mixture filters out unwanted UV radiation. Upon completion of the photooxygenation, the solution is warmed to room temeperature and the solvent is removed under vacuum to yield arginine dioxetane 9.

3-Methoxyspiro[1,2-dioxetane-3,2'tricyclo[3.3.1.1³,⁷]decan]-4-yl)-1-anilinyl-L-Arg-Ala-N-Cbz (10). N-Cbz-Ala-Arg dioxetane 10 is synthesized from enol ether 6 as described for compound 9.

3-Methoxyspiro[1,2-dioxetane-3,2'tricyclo[3.3.1.1³,⁷]decan]-4-yl)-1-anilinyl-L-Ara-Gly-Gly-N-Cbz (11). N-Cbz-Gly-Gly-Arg-dioxetane 11 is synthesized from enol ether 7 as described for compound 9.

3-Methoxyspiro[1,2-dioxetane-3,2'tricyclo[3.3.1.1³,⁷]decan]-4-yl)-1-anilinyl-L-Ara-Gly-Val-N-Cbz (12). N-Cbz-Val-Gly-Arg-dioxetane 12 is synthesized from enol ether 8 as described for compound 9.

3-Methoxytricyclo[3.3.1.1³,⁷]dec-2-ylidenemethyl)-1-anilinyl-Ala-Ala-N-Cbz (13). Enol ether aniline 1 (68 mg, 0.25 mmol) was dissolved in 0.6 ml anhydrous dimethylformamide and 0.6 ml anhydrous pyridine under argon. N-Cbz-Ala-Ala (92 mg, 0.31 mmol), 1-[3-(dimethylamino)propyl]-3-ethylcarbodiimide HCl (59 mg, 0.31 mmol) and a crystal of 1-hydroxybenzotriazole were added under argon at room temperature. The reaction was stirred for 2 hr, partitioned between ethyl acetate and water, and the organic layer was washed successively with dilute brine and dilute sodium bicarbonate solutions. The organic layer was dried over Na₂SO₄, evaporated and purified on a silica gel column (25–75% EtOAc/hexanes) to yield 134 mg (97%) of enol ether peptide 13.

¹H NMR (CDCl₃, ppm): 1.35–1.42 (6H, m); 1.5–2.3 (12H, m); 2.61 (1H, br s); 3.21 (1H, br s); 3.26 (3H, s); 4.15–4.32 (1H, m); 4.62–4.70 (1H, m); 5.09 (2H, s); 5.5 (1H, br s); 6.8 (1H, br s); 7.02 (1H, d, J=7.6 Hz); 7.30 (5H, m); 7.2–8.0 (4H, m).

3-Methoxytricyclo[3.1.1.1³,⁷]dec-2-ylidenemethyl)-1-anilinyl-Ala-Ala (14). Enol ether 13 (28.7 mg, 0.05 mmol) was dissolved in 1 ml absolute EtOH. Palladium on carbon catalyst (5%, 33 mg) and 1,4-cyclohexadiene (40 μl, 0.5 mmol) were added and the reaction was heated stirring at 55° C. for 40 min. The solution was filtered through a celite plug to remove catalyst and evaporated to yield 18 mg of 14 as clear oil. The crude oil was used without further purification for subsequent peptide couplings.

3-Methoxytricyclo[3.3.1.1³,⁷]dec-2-ylidenemethyl)-1-anilinyl-(Ala)₃-N-Ac (15). N-Ac-(Ala)₃ enol ether 15 is synthesized by coupling (Ala)₂-enol ether 14 with N-acetyl-L-Ala as described for compound 13.

3-Methoxytricyclo[3.3.1.1³,⁷]dec-2-ylidenemethyl)-1-anilinyl-(Ala)₄-N-Cbz (16). N-Cbz-(Ala)₄-enol ether 16 was synthesized by coupling (Ala)₂-enol ether 14 (18 mg, 0.04 mmol) with Ala-Ala-N-Cbz (14 mg, 0.48 mmol) as described for compound 13.

3-(4-Methoxyspiro[1,2-dioxetane-3,2'tricyclo[3.3.1.1³,⁷]decan]-4-yl)-1-anilinyl-Ala-Ala-N-Cbz (17). N-Cbz-Ala-Ala-dioxetane 17 is synthesized from enol ether 13 as described for dioxetane 3.

3-(4-Methoxyspiro[1,2-dioxetane-3,2'tricyclo[3.3.1.1³,⁷]decan]-4-yl)-1-anilinyl-(Ala)₃-N-Ac (18). N-Ac-(Ala)₃-dioxetane 18 is synthesized from enol ether 15 as described for dioxetane 3.

3-(4-Methoxyspiro[1,2-dioxetane-3,2'tricyclo[3.3.1.1³,⁷]decan]-4-yl)-1-anilinyl-(Ala)₄-N-Cbz (19). N-Cbz-(Ala)₄-dioxetane 19 is synthesized from enol ether 16 as described for dioxetane 3.

Scheme 1. Synthesis of Protease Dioxetane Substrate

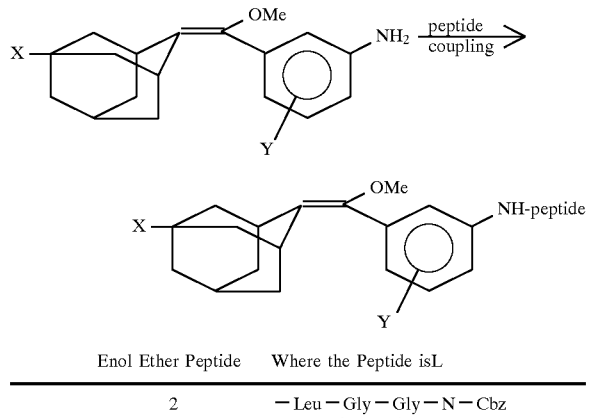

| Enol Ether Peptide | Where the Peptide isL |
| --- | --- |
| 2 | —Leu—Gly—Gly—N—Cbz |
| 4 | —Arg-tri-N—Cbz |
| 5 | —Arg |
| 6 | —Arg—Ala—N—Cbz |
| 7 | —Arg—Gly—Gly—N—Cbz |
| 8 | —Arg—Gly—Val—N—Cbz |
| 13 | —Ala—Ala—N—Cbz |
| 14 | —Ala—Ala |
| 15 | —(Ala)₃—N—Ac |
| 16 | —(Ala)₄—N—Cbz |

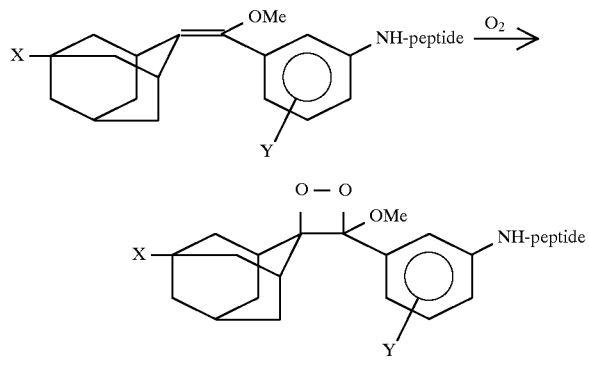

| Dioxetane Peptide | From Enol Ether | Where the Peptide is: |
| --- | --- | --- |
| 3 | 2 | —Leu—Gly—Gly—N—Cbz |
| 9 | 5 | —Arg |
| 10 | 6 | —Arg—Ala—N—Cbz |
| 11 | 7 | —Arg—Gly—Gly—N—Cbz |
| 12 | 8 | —Arg—Gly—Val—N—Cbz |
| 17 | 13 | —Ala—Ala—N—Cbz |
| 18 | 15 | —(Ala)₃—N—Ac |
| 19 | 16 | —(Ala)₄—N—Cbz |

Where X, Y=H, Cl, Br, l, F OMe, OH, OR, alkyl, COOR, CONHR, CONR2, etc. Where Cbz=N-Carbobenzoxy and Ac=N-acetyl

CHEMILUMINESCENT ASSAY FOR SUBTILISIN

Subtilisin is a thermally stable enzyme capable of withstanding 60° C. temperatures. It is also tolerant of salts and resistant to urea/detergent denaturation.

Protocol

Experiment 1

Protease substrate 3 (0.1 mM in 0.05 M Tris, pH 8.5, 10% acetonitrile) was incubated at 30° C. in a Turner TD-20e Luminometer. After recording the background emission for approximately 4.5 minutes, 1μ, of 20 mg/mL protease (Subtilisin Carlsberg, Sigma P5380) was added and the light emission was measured. The background was measured on the 0–10 scale. Upon addition of enzyme, the scale was changed to the 0–100 scale and later (around 9 minutes) to 0–1000. The results of this experiment are shown in FIG. 1.

Experiment 2

Protease (Subtilisin Carlsberg Sigma P5380) was serially diluted and added to 0.1 mM protease substrate 3 in 0.05 M Tris, pH 8.5 containing 10% acetonitrile, 1 mg/mL Sapphire, or 0.1% Pluronic F127. The following concentrations of protease were tested in duplicates (100 μL per well): 200, 20, 2, 0.2, and 0.02 μg per mL. The microtiter wells were then incubated at 37° C. for 1 hour and the chemiluminescent signal was measured in a Dynatech ML2250 Microtiter plate luminometer. The plate was then incubated for another hour at 45° C., and the chemiluminescent signal was again measured. The results of this experiment are shown in FIG. 2 (37° C.) and FIG. 3 (37° C. followed by 45° C.).

As shown by the above experiment, digestion of the peptide moiety Z by the enzyme results in spontaneous decomposition and chemiluminescence. One particular application, by no means intended to be limiting to the invention, embraces DNA detection in solution, and DNA blot assays, using thermophilic enzymes such as thermolysin. The preparation of DNA materials frequently requires high temperature processes, including denaturation and PCR amplification. It would be advantageous to affix the enzyme label to the DNA in advance of these high temperature processes, and have the label carried forward. Many enzymes, however, are deactivated and denatured by exposure to high temperatures, and accordingly, complex post-amplification coupling requirements are frequently used. As the novel dioxetanes of the claimed invention function as excellent substrates for thermolysin and other thermophilic enzymes, this invention finds particular application to DNA detection, and DNA hybridization assays. In particular, DNA probes and DNA samples can be prepared with the thermophilic enzyme affixed, subjected to denaturation and amplification, subsequently prepared in solution or deposited on a membrane, subjected to stringent hybridization conditions, and still retain the enzyme label which will activate the dioxetane substrate reporter molecule of the invention.

Other assay formats familiar to those of skill in the art can be employed in connection with the claimed invention. In addition to single, solution phase assays for the presence of a particular enzyme, labels can be attached via covalent bonding, to special or high-affinity bonding ligands, such as antibodies, antigens and ligand pairs such as avidin or stretavidin-biotin bonding pairs. Thus, in addition to DNA hybridization assays, DNA solution assays, enzyme assays, other conventional assays including immunoassays and specific solution assays can be practiced within the claimed invention.

Figure 2A:
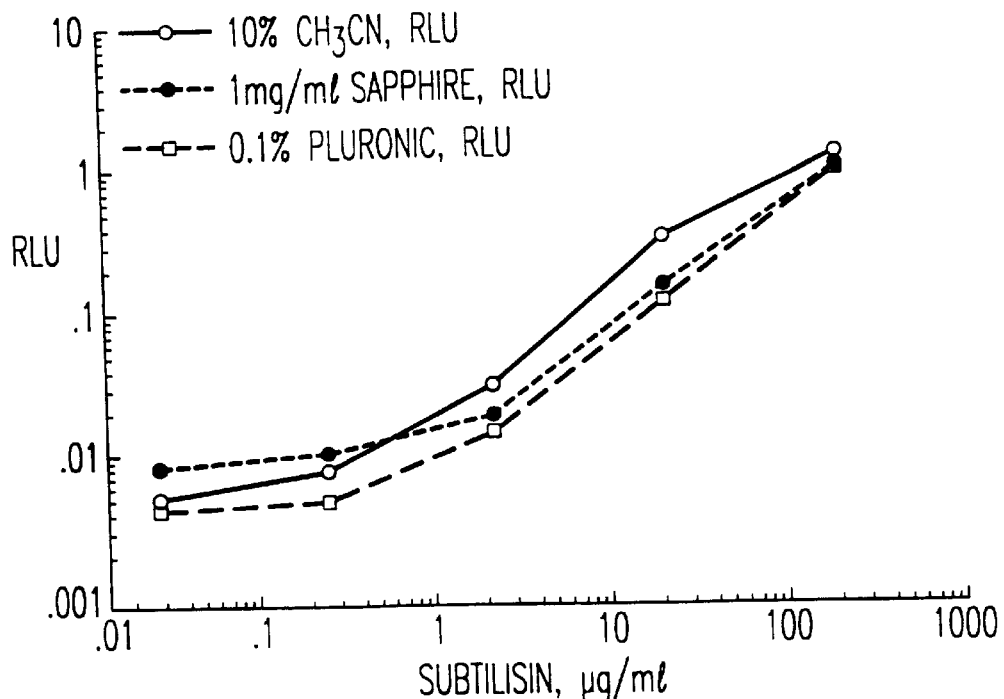
FIG. 2A is presented in light units, while FIG. 2B provides a measure of the signal-to-noise (S/N) ratio.
Figure 2B:
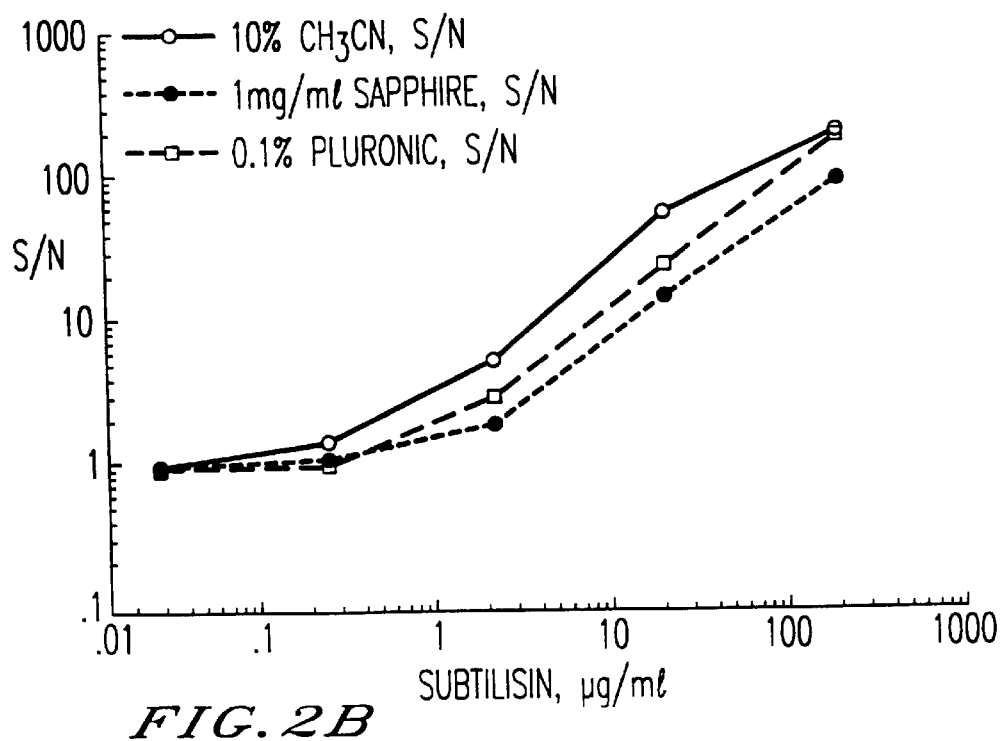
FIG. 2. A graph reflecting the chemiluminescent signal obtained by triggering 1,2-dioxetane substrate for subtilisin with serial dilutions of subtilisin at 37° C.
Figure 3A:
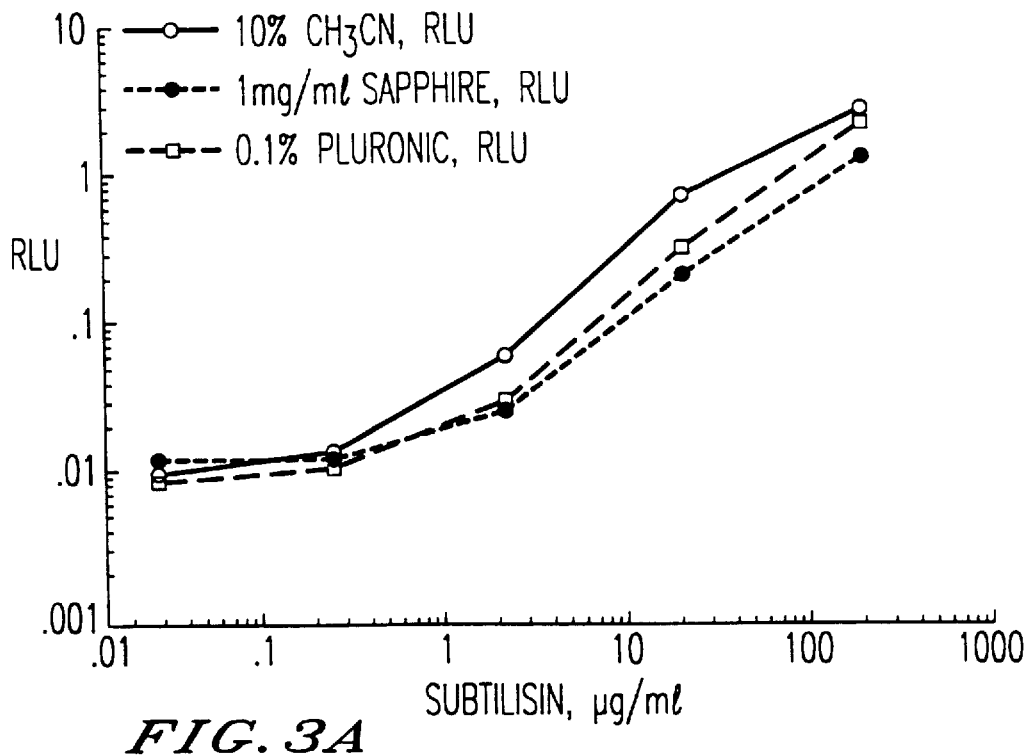
FIG. 3.
Figure 3B:
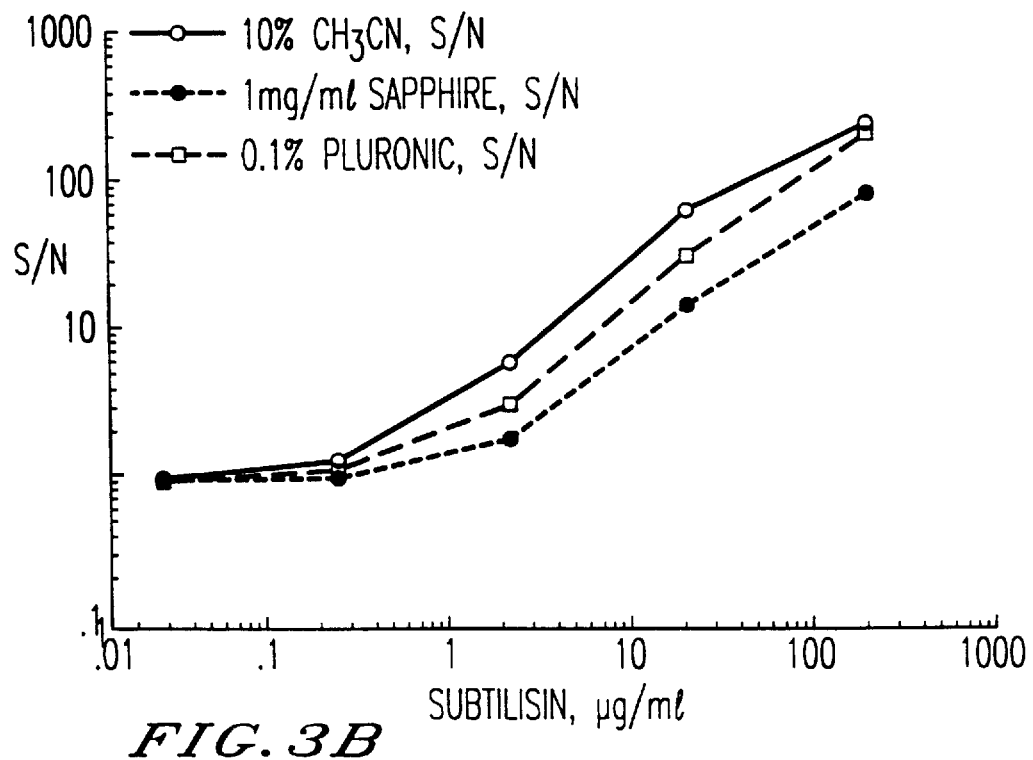

Additionally, as illustrated in FIGS. 2 and 3, a wide variety of enhancement agents can be used to improve chemiluminescent performance. Representative enhancement agents, such as those set forth in U.S. Pat. No. 4,978,614 are typically water-soluble macromolecules, which may be naturally occurring substances, such as albumin, or a polymeric quaternary onium salt, including phosphonium, sulfonium and ammonium salts. Exemplary enhancement agents are disclosed in U.S. Pat. No. 5,145,772, and U.S. Pat. No. 5,112,960, including poly (vinylbenzyltrimethylammoniumchloride) (TMQ), poly (vinylbenzyltributylammoniumchloride) (TBQ) and poly (vinylbenzyldimethylbenzylammoniumchloride) (BDMQ). These particular polymers act to sequester the hydrophobic dioxetane amine, excluding water, which tends to dampen or "quench" dioxetane chemiluminescence. Further improvements can be obtained by using an enhancement additive which further improves the ability of these enhancement agents to form hydrophobic regions, particularly surfactants, negatively charged salts, alcohols, turpentines and other solvents, and water-soluble polymers. Typical enhancement effects obtained through this method are disclosed in pending U.S. patent application Ser. No. 08/031,471, which is incorporated herein by reference. Where a blotting assay, or other membrane-based assay is to be practiced, chemiluminescent performance, and S/N ratio, as well as sensitivity, can be further enhanced by using membranes coated with a polymer coating, including those disclosed in U.S. Pat. No. 5,336,596, which is incorporated herein by reference. Suitable supports for the polymer coating include nitrocellulose, nylon and PVDF.

As noted above, the dioxetane amine remaining after removal of the protease-labile moiety is akin to the oxyanion of aryloxy-substituted dioxetanes of the prior art, in that it spontaneously decomposes and chemiluminesces. The dioxetane amine-based assay may be improved by gentle heating of the solution or sample comprising the dioxetane amine. The dioxetanes of this invention are particularly stable, and accordingly, gentle heating should not give rise to substantial increases in the spontaneous emission of light caused by thermally induced decomposition. Other elements of the sample, that is, the elements of the sample being inspected, including the target analyte, will generally establish the limits as to what range of elevated temperatures may be employed. The dioxetanes and assays of this invention employ proteases, which are generally subject to denaturing and/or activity reduction at elevated temperatures (although some are resistant to most conventional temperatures) and frequently find important applications in the inspection of biological samples and detection of analytes which may additionally be heat sensitive. A generally recognized temperature limit for biological material is 100° F. Accordingly, where the assay employs biological materials, heating above 100° F. should be avoided. A generally preferred range is 45°–65° F. Heating at temperatures between ambient temperatures and 45° F. may realize a more modest increase in reaction speed.

This invention has been disclosed in terms of both generic description and specific example. Variations will occur to those of ordinary skill in the art, including peptide moiety identities, specific proteolytic enzymes to be employed, enhancement agents and enhancement additives, and specific assay formats without the exercise of inventive faculty. Such variations remain within the scope of the invention, save for variations excluded by the recitation of the claims presented below.

What is claimed is:
1. A compound of the formula

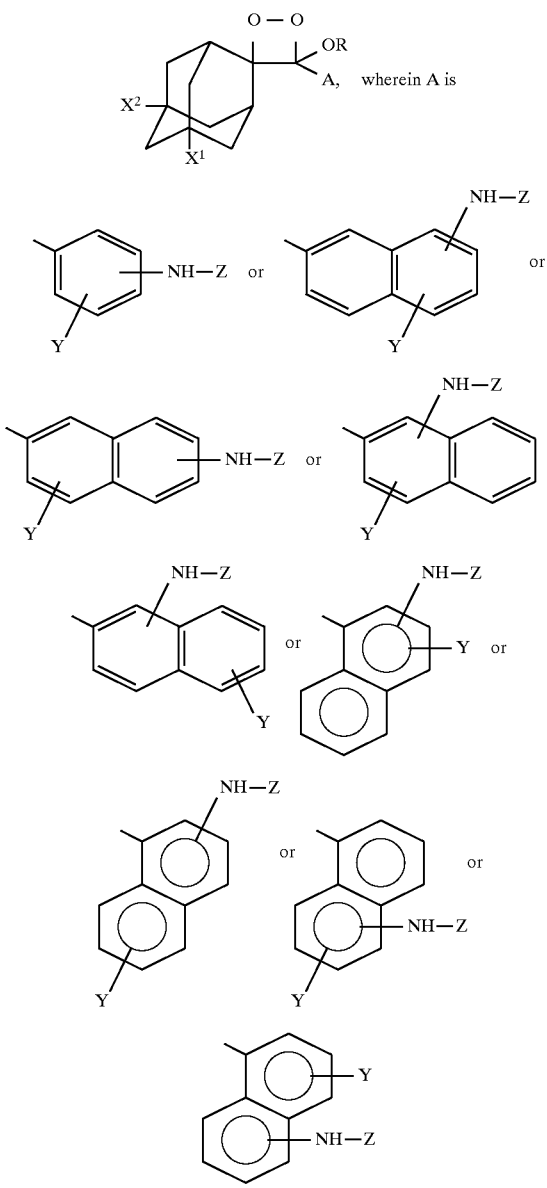

wherein $X^1$, $X^2$ and Y are independently hydrogen or an electron donating or withdrawing substituent, wherein R is an alkyl, straight-chain or branched chain of 1–20 carbon atoms or cycloalkyl or polycycloalkyl of 3–20 carbon atoms, and wherein Z is selected from the group consisting of Cbz-Val-Lys-Met-, Arg-, Ala-, Ala-Ala-Phe-, Glu-, Gly-Pro-Leu-, Gly-Pro-Met-, Leu-, Cbz-Arg-Arg-, Cbz-Phe-Arg-, Bz-Arg-, Suc-Ala-Ala-Pro-Phe, Cbz-Ala-Arg-Arg-, Gly-Phe-, Ala-Arg-, Bz-Arg-Gly-Leu-, Gly-Arg-, Bz-Arg-Gly-Phe-Phe-Pro-, Suc-Ala-Ala-Phe-, Suc-Phe-Leu-Phe-, Suc-Val-Pro-Phe-, MeOSuc-Ala-Ala-Pro-Met-, Ac-Ala-Ala-Ala, Suc-Ala-Ala-Ala-, Boc-Ala-Ala-Ala-, Suc-Ala-Ala-Val-, Suc-Ala-Pro-Ala-, Ac-Ala-Pro-Ala-, Suc-Ala-Ala-Pro-, Ac-Ala-Ala-Pro-Ala-, Boc-Ala-Ala-Pro-Ala-, Glu-Ala-Ala-Pro-Leu-, Suc-Ala-Ala-Pro-Met-, MeOSuc-Ala-Ala-Pro-Val-, Boc-Ala-Ala-Pro-Val-. Suc-Leu-Leu-Val-Tyr-, Pro-Phe-Arg-, Cbz-Gly-, Cbz-Gly-Gly-Leu-, Cbz-Ala-Ala-Leu-, Boc-Gly-Gly-Leu-, Abz-Ala-Ala-Phe-Phe-, Cbz-Phe-Pro-Arg-, Cbz-Gly-Gly-Arg-, Bz-Val-Gly-Arg-, Boc-Val-Gly-Arg-, Glt-Gly-Arg-, Gly-Arg-, Cbz-Val-Gly-Arg-, wherein Abz is 2-aminobenzoyl, Ac is acetyl, Bz is benzoyl, Glt is glutaryl, Suc is succinyl, Cbz is carbobenzoxy, Abu is 2-aminobutyric acid and, pyr is pyroglutamic acid.

2. The compound of claim 1, wherein at least one of $X^1$, $X^2$ and Y is an electron donating or withdrawing group, and is further selected so as to be a solubilizing group for rendering said compound more soluble in aqueous preparations.

3. The compound of claim 1, wherein $X^1$ and $X^2$ are, individually hydrogen, a hydroxyl, a halogen, a hydroxy lower alkyl group, a halo lower alkyl group, a phenyl group, a halo phenyl group, an alkoxyphenyl group, a hydroxyalkoxy group, a cyano group or an amide group.

4. The compound of claim 1, wherein Y is hydrogen, chloro, alkoxy, aryloxy, trialkylammonium, alkylamido, arylamido, arylcarbamoyl, alkylcarbamoyl, cyano, nitro, ester, alkyl-or arylsulfonamido, trifluoromethyl, aryl, alkyl, trialkyl-, triaryl, or alkylarylsilyl, alkyl- or arylamidosulfonyl, alkyl- or arylsulfonyl and alkyl-or arylthioether.

5. The compound of claim 2, wherein said solubilizing group is selected from the group consisting of an ammonium group, a phosphonium group, a sulfonium group, a carboxylic acid group, a sulfonic acid group, a trifluoromethylsulfonyl group, a methylsulfonyl group, a cyano group and a hydroxy group.

6. The compound of claim 1, wherein at least one of $X^1$ and $X^2$ is chloro, and Y is chloro or methyl.

7. The compound of claim 1, wherein A is

8. The compound of claim 1, wherein A is naphthyl, and the moiety NH-Z is at a disjoint substitution position with respect to the point of attachment to the dioxetane ring.

9. A method of detecting the presence and/or amount of a protease in a sample, comprising adding the compound of claim 1 to said sample, incubating said sample and inspecting said sample for the generation of light, wherein light so generated is indicative of the presence and/or amount of said protease wherein Z is a substrate for which said protease is specific.

10. The method of claim 9, wherein said protease is bound to DNA.

11. The method of claim 9, wherein said protease is bound to an antibody.

12. The method of claim 9, wherein said protease is bound to a substance for which an antibody is specific.

13. The method of claim 9, wherein said protease is bound to avidin or streptavidin-biotin bonding pairs.

14. A kit for the detection of a protease by generation of chemiluminescence, comprising a compound of claim 1 and a membrane on which an assay for said detection of a protease employing said compound is conducted.

15. A kit for conducting an assay to determine the presence and/or amount of a protease in a sample comprising a compound of claim 1, and a substance which enhances the amount of light released by the removal of moiety Z from said compound, as compared with the amount of light generated by the removal of moiety Z in the absence of said enhancer.

16. The kit of claim 15, wherein said kit further comprises a membrane on which said assay is conducted.

* * * * *